United States Patent [19]

Oman et al.

[11] Patent Number: 4,723,554
[45] Date of Patent: Feb. 9, 1988

[54] SKIN PALLOR AND BLUSH MONITOR

[75] Inventors: Charles M. Oman, Winchester; Walter J. C. Cook, Malden, both of Mass.

[73] Assignee: Massachusetts Institute of Technology, Cambridge, Mass.

[21] Appl. No.: 898,740

[22] Filed: Aug. 15, 1986

Related U.S. Application Data

[63] Continuation of Ser. No. 604,908, Apr. 27, 1984, abandoned.

[51] Int. Cl.$^4$ ............................................. A61B 5/02
[52] U.S. Cl. .................................. 128/664; 128/633; 128/666; 128/690; 250/238
[58] Field of Search ............... 128/690, 633, 634, 664, 128/667; 250/238

[56] References Cited

U.S. PATENT DOCUMENTS

4,013,067  3/1977  Kresse et al. .................... 128/666

Primary Examiner—William E. Kamm
Assistant Examiner—John C. Hanley
Attorney, Agent, or Firm—James E. Maslow; Thomas J. Engellenner

[57] ABSTRACT

A new type of infrared reflectance device is disclosed to provide a quantitative evaluation of skin pallor. The instrument is designed to produce a measurement proportional to the percentage of infrared reflectance of the skin. In one embodiment, it consists of a miniature GaAs light emitting diode, which provides a pulsed infrared light source, a silicon photodiode detector, and processing circuitry. The device electronics are temperature compensated and are designed to respond only to the pulsed component of the detector output and to reject components due to stray light from external sources. The wavelength is chosen such that the measurement is relatively insensitive to the level of blood oxygenation and melanin pigment in the skin.

13 Claims, 17 Drawing Figures

SKIN PALLOR AND BLUSH MONITOR

The Government has rights in this invention pursuant to Contract Number NCC 9-1 awarded by the National Aeronautics and Space Administration.

This application is a continuation, of application Ser. No. 604,908, filed Apr. 27, 1984, now abandoned.

BACKGROUND OF THE INVENTION

This invention relates to the field of biomedical instrumentation and, in particular, to reflectance-mode blood circulation monitors.

Measurements of skin pallor are particularly useful in physiological diagnoses and the monitoring of patients. Changes in skin pallor are recognized as cardinal signs of motion sickness, nausea, and shock, and presumably are due to changes in the volume of blood in the microcirculation of the skin. Assessing these changes in peripheral vascular activity using a light source and a photodetector is known as reflectance-mode photoplethsmography.

Attempts have been made to measure blood circulation through skin, employing tungsten lamps and photoconductive cells but several problems have prevented these devices from producing a signal proportional to the total blood volume. Temperature sensitive photocell detectors produce a hysteresis related to prior light exposure. Additionally, relative motion between the transducer and the skin generates artifactual outputs as a result of distance variations between the transducer and skin or compression of the dermal blood vessels. As a result, prior art devices have measured only blood volume pulse amplitude (BVP) rather than absolute reflectance (pallor). Moreover, when visible light is utilized, the BVP devices typically cannot be used on dark skinned individuals and artifactual light components (arising from the ambient environment) seriously degrade the signal.

The deficiencies of the tungsten lamp/photocell designs have led designers to suggest the use of solid-state infrared LED/silicon phototransistor and photodiode devices as photoplethysmographic instruments. Unfortunately, such devices also are sensitive to the infrared components of room and natural lighting. Moreover, the LED light source output can vary with temperature, and motion artifacts can still be present.

Devices which can accurately measure skin pallor will find applications in a variety of cardiovascular and neurological diagnoses. In particular, devices which can provide monitoring of either acute or ambulatory illnesses by detecting changes in skin pallor can satisfy a long-felt need. Additionally, such devices can be useful in detecting and analyzing particular circulatory ailments, such as Raynaud's syndrome which apparently is caused by occupational exposure to vibration and results in reduced vascular circulation in the extremities of those afflicted.

Therefore, there exists a need for devices to monitor skin pallor and preferably, skin temperature, BVP and heart rate as well. Such devices should provide ambient light cancellation and compensate for temperature variations in the LED light source. Such devices should also minimize motion artifacts.

SUMMARY OF THE INVENTION

A new type of infrared reflectance device is disclosed to provide a quantitative evaluation of skin pallor. The instrument is designed to produce a measurement proportional to the absolute infrared reflectance of the skin. In one embodiment, it consists of a miniature GaAs light emitting diode, which provides a pulsed infrared light source, a silicon photodiode detector, and processing circuitry. The device electronics are temperature compensated and are designed to respond only to the pulsed component of the detector output and to reject components due to stray light from external sources. The wavelength is chosen such that the measurement is relatively insensitive to the level of blood oxygenation and melanin pigment in the skin.

Additional features of the device include: circuits to extract average blood volume pulse amplitude (BVP) and heart rate information, radiometrically calibrated measurements in physical units, and an adjustable source pulse amplitude to standardize the amount of light reflected back to the detector so that the device works equally well on both dark and light skinned individuals.

Motion sickness test data obtained from individual human subjects employing the invention while making head movements in a rotating chair or while wearing left-right vision reversing goggles revealed a consistent pattern on onset and remission of facial pallor. Changes in pallor measured by the invention were correlated with changes in skin temperature measured close by on the face. Prototype devices according to the present invention have also been flown on U.S. space shuttle missions.

The present invention will find practical use in hospital applications, particularly during surgical operations and in recovery and intensive care units to indicate the onset of shock, nausea, syncope and related illnesses. Additionally, the invention may be useful as a diagnostic tool in evaluating cases of Raynaud's syndrome and other circulatory disorders.

DESCRIPTION OF THE PREFERRED EMBODIMENTS

Figure 1:
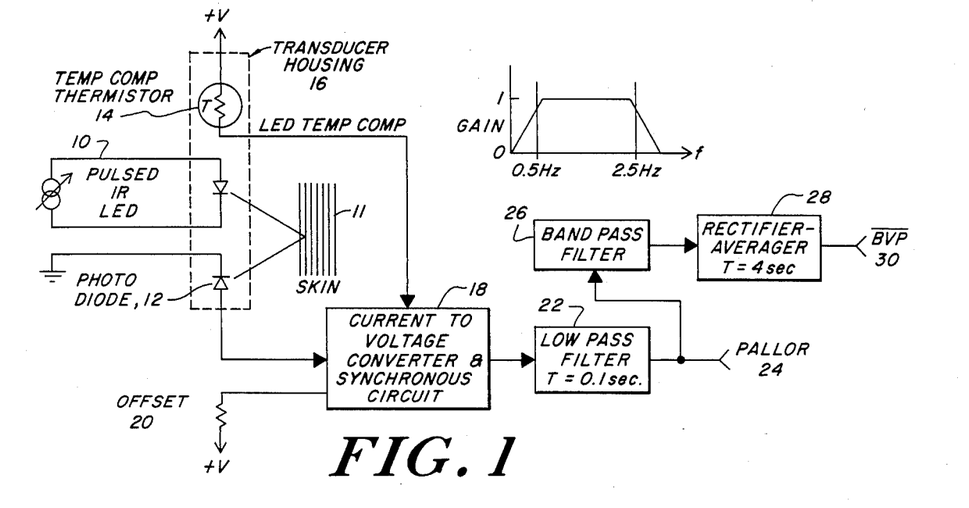
FIG. 1 is a schematic block diagram of the pulsed infrared reflectance system for monitoring pallor.

Referring first to FIG. 1, one embodiment of the invention consists of an infrared light emitting diode (LED) 10 to provide a source of infrared light which is reflected from within the tissues of a patient's skin 11 and onto a photodiode 12. The signal is pulsed to identify the signal apart from ambient light. A temperature compensating thermistor 14 is employed in the transducer housing 16 to correct for the effect of temperature changes on the emitted power of the LED. A current-to-voltage converter and synchronous demodulator circuit 18 amplifies the photodiode signal utilizing an offset 20 to keep the pallor signal from saturating subsequent stages of circuitry. A low pass filter 22 can be utilized to reduce noise in the output pallor signal. This signal can also be used to produce the average blood volume pulse amplitude (BVP) 30 signal by utilizing a band pass filter 26 (i.e., between 0.5 and 2.5 Hz) and a rectifier-averager 28.

Figure 2:
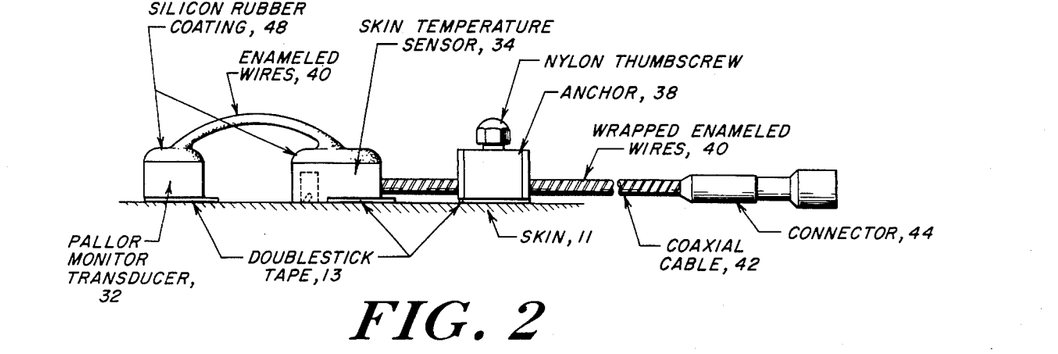
FIG. 2 is a detailed side view of the probe components of the invention as attached to the skin.

FIG. 2 is a side view of a probe assembly which consists of the pallor monitor transducer 32 and skin temperature sensor 34 joined together by enameled wires 40. This assembly is linked by cable 42 to a connector 44, by which the transducer and temperature signals are communicated to the synchronous circuitry (discussed below). Motion artifacts due to pulling and twisting of the cable are further minimized with an anchor 38 which can be mounted, for example, below the patient's chin using double stick tape 13. The transducer 32 and skin temperature sensor 34 can also be joined to the skin 11 with double stick micropore tape 13 to further minimize motion artifacts. Approximately one square centimeter of double-stick tape is sufficient to secure each component with the transducer preferably mounted at an edge rather than the center of the tape to minimize blushing artifacts. The transducer 32 can be directly applied to tape and will function satisfactorily because the tape is transparent in the infrared region.

Figure 3A:
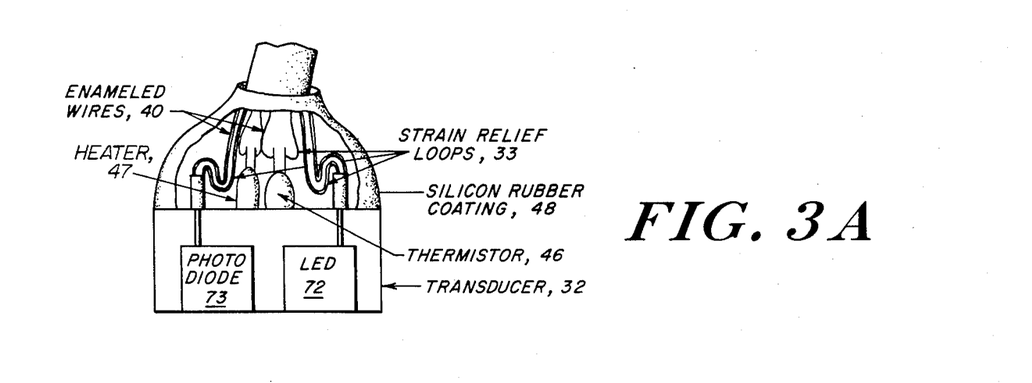
FIG. 3a is a detailed side view of the electro-optical transducer, the temperature compensating thermistor, and the associated wiring connections.

FIG. 3a is a detailed drawing of the pallor monitor transducer 32 and its associated electrical components. In the illustrated embodiment, the transducer 32 is a reflective electro-optical solid state switch, such as the Spectronics SPX5004-1 transducer which emits and collects the pulsed infrared light to produce the skin pallor and peak BVP signals. The transducer 32 consists of a miniature GaAs light emitting diode (LED) infrared light source 72 and a silicon photodiode detector 73 with red filter in a plastic housing. A thermistor 46 is also employed to compensate for LED temperature changes. A heater element 47 can be employed to maintain nearly constant the temperature of the LED 72. The pulse signals, reflected signals, and temperature signals for the transducer 32 are carried to the device electronics by wires 40 (i.e., #36 AWG enameled wires). Each enameled wire 40 can be installed with a strain relief loop 33 within the coating 48 to resist breakage. The wires should also be flexible so as to minimize the mechanical compression of the dermal microvessels and thereby to reduce "artifactual" pallor due to skin motion. A silicon rubber coating 48, such as Dow Corning RTV3140, can be used to enclose the connections.

Figure 3B:
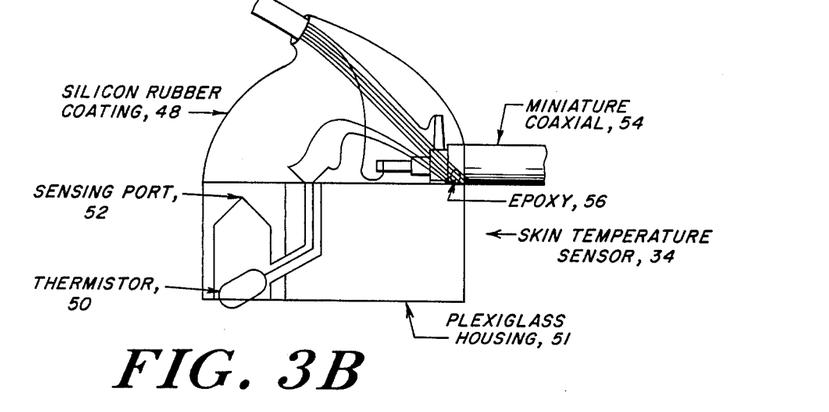
FIG. 3b is a detailed side view of the skin temperature thermistor and its attachment block.

FIG. 3b is a detailed drawing of a skin temperature sensor 34 which can be used in conjunction with the pallor monitor. Again, a thermistor 50 is employed to provide an appropriate skin temperature signal. The thermistor 50 is mounted in sensing port 52 within a plexiglass housing 51. Preferably, the thermistor 50 should contact the skin directly and in the illustrated embodiment using double stick tape 13, the thermistor extends beyond the edge of the tape 13. The housing 51 shields the thermistor 50 from ambient air and radiation. A miniature coaxial wire 54 is secured to the plexiglass housing 51, for example by epoxy 56 and, again, a silicon rubber coating 48 can enclose sensor 34 and the end of the miniature coaxial wire 54. In the illustrated embodiment, the photodiode leads are connected to the coaxial cable 54 while the skin thermistor wires, the LED temperature-compensating thermistor wires and the LED pulse signal wires can be wrapped about the outside of the coaxial cable 54.

Figure 3C:
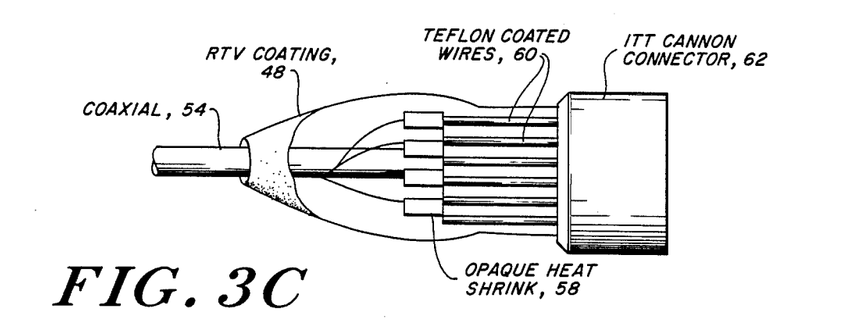
FIG. 3c is a detailed side view of the probe cable connector assembly.

FIG. 3c is a detailed drawing of a side view of the probe cable connector assembly to the main housing. The enameled wires 40 are wrapped around the miniature coaxial cable 54 and protected by the RTV coating 48. At the connector interface, the enameled wires 40 are joined to the 6 teflon-coated wires 60 and surrounded by opaque heat shrink 58. (One wire from each thermistor is joined together to a common line in connector 62). The teflon-coated wires 60 are an integral part of the ITT Cannon connector 62 which interfaces to the electronic circuitry of the invention.

Figure 4:
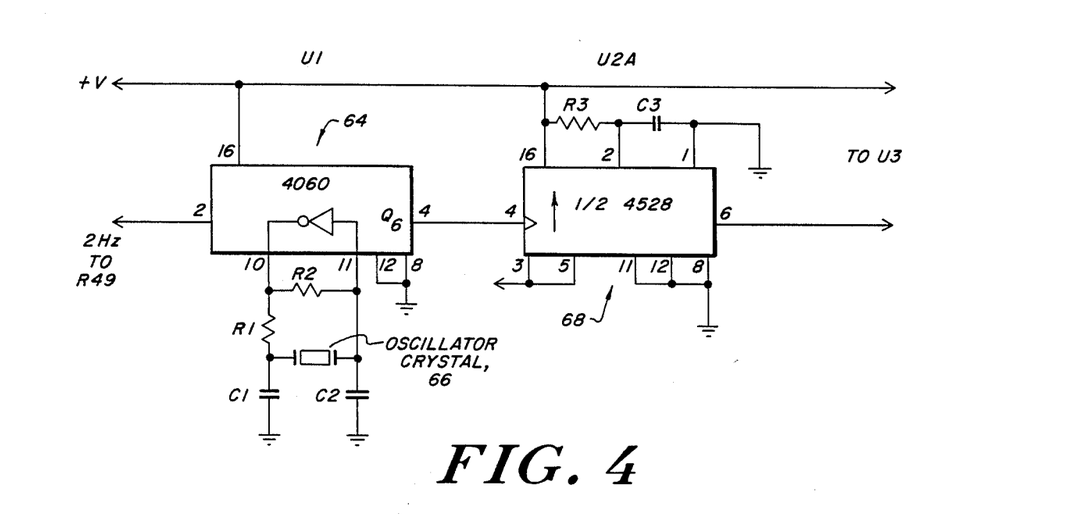
FIG. 4 is a schematic diagram of the timing circuitry of the system shown in FIG. 1.

In FIG. 4 an illustrative timing circuit is shown comprising a standard 4060 National ("U1") integrated circuit chip 64 and a 16 kHz oscillator crystal 66 which produces a 250 Hz rectangular pulse at pin 4 of the integrated circuit U1, designated as U1-4, with the appropriate selection of resistors R1 and R2 and capacitors C1 and C2. The 250 Hz rectangular waveform from U1-4 has a 4 ms period pulse with a 50% duty cycle and a peak voltage of 5.8 V. The source of this +5.8 V voltage is supplied to U1-16 and a 2 Hz output at U1-2 is used to pulse the battery level detection circuitry. (Both the power supply and the battery level detection circuitry are discussed in detail below).

The ouput from U1-4 is received by a 4528 National ("U2A") integrated circuit chip 68 which is a one-shot monostable multi-vibrator. The 4528 IC chip 68 converts the rectangular waveform at U2A-4 from a 4 ms period, 2 ms pulse (50% duty cycle) to a 4 ms period, 0.2 ms pulse (5% duty cycle) at the output U2A-6. The purpose of such a reduction in the duty cycle is to reduce the power consumption when restrictions of size and power levels exist. Resistor R3 and capacitor C3 are chosen to convert the 50% duty cycle at U2A-4 to the 5% duty cycle driving pulse at U2A-6. It is important to note that the 0.2 ms pulse is not critical and the selection of the pulse duty cycle may be varied with the appropriate selection of Resistor R3 and Capacitor C3 as long as the frequency of the driving pulse is not too close to a harmonic of 60 Hz.

Figure 5:
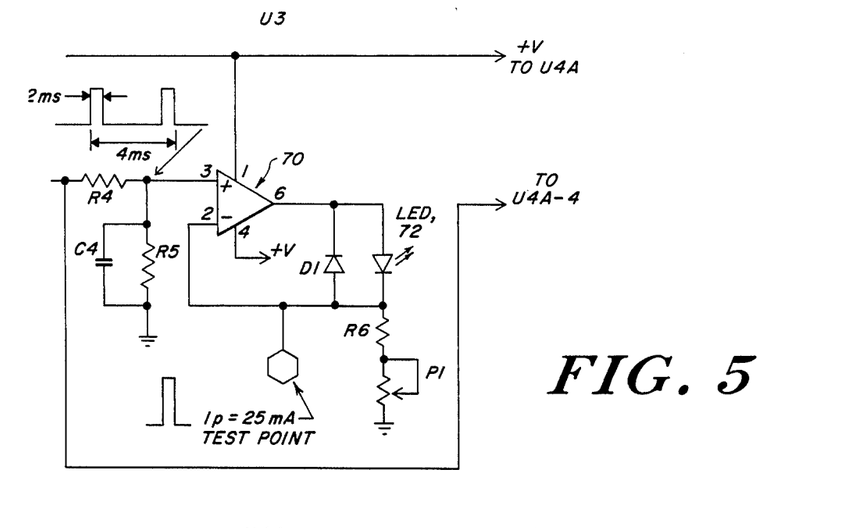
FIG. 5 is a schematic diagram of the current regulator and pulsed LED of FIG. 1.

In FIG. 5 a schematic diagram of a current regulator and its relationship to the LED 72 of transducer 32 is shown. The regulator comprises a Harris HA2-2705-5 ("U3") integrated circuit chip 70 and appropriate capacitors and resistors. Because the LED 72 typically has a temperature dependent resistance of approximately −8 ohm/10° C., a voltage source, if used, would therefore produce a higher power output as the LED 72 increased in temperature over time. However, the current regulator prevents small changes in the LED resistance from affecting the power output from the LED 72. The resistors R4 and R5 reduce the 0.2 ms pulse amplitude of the −5.8 V at the output U2A-6 in FIG. 4 to a +1.8 V 0.2 ms pulse. The U3 chip 70 converts this 0.2 ms waveform into a 25 mA peak 0.2 ms waveform at the LED with the appropriate selection of Resistor R6. Potentiometer P1 which sets peak LED current is utilized to adjust for variation in skin pigment content thereby achieving a standardized output and detection level regardless of melanin and baseline hemoglobin content in the skin.

Figure 6A:
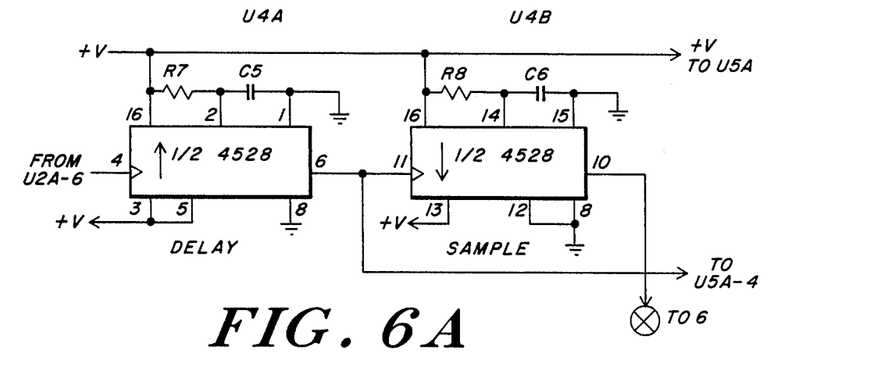
FIG. 6a is a schematic diagram of the LED on sampling circuitry.
Figure 6B:
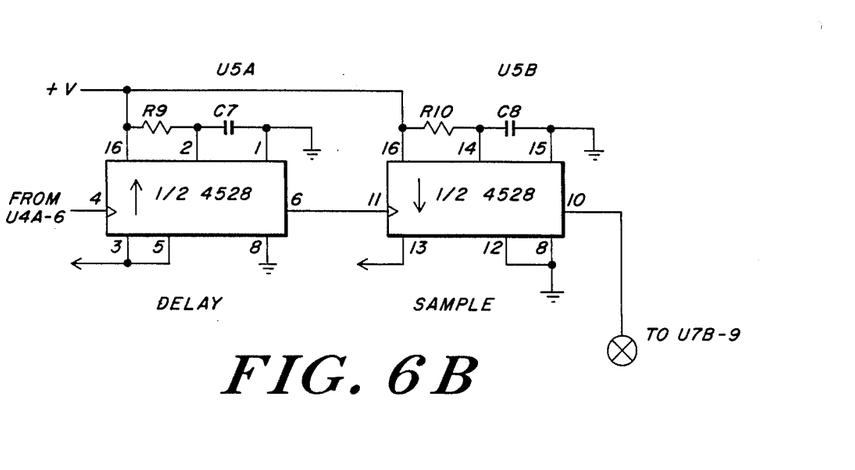
FIG. 6b is a schematic diagram of the LED off sampling circuitry.
Figure 6C:
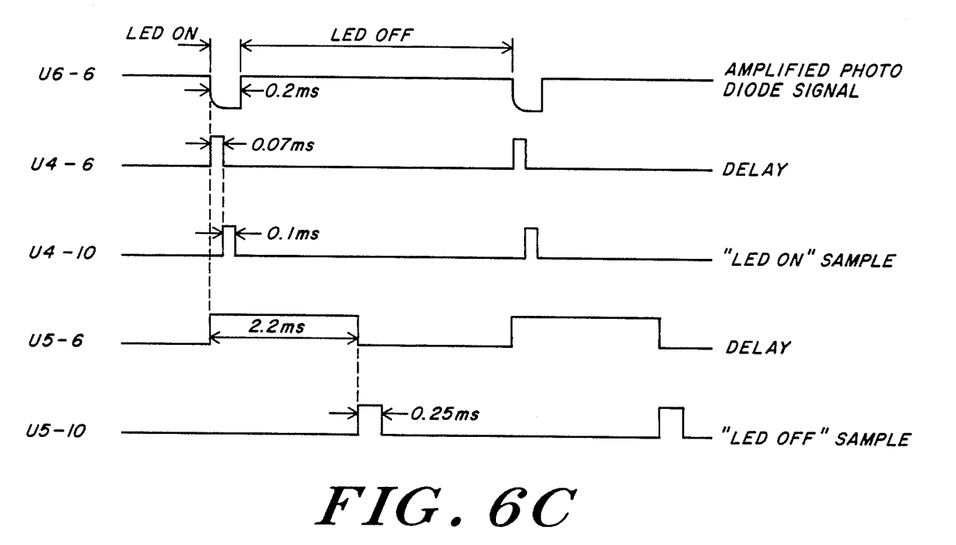
FIG. 6c is a timing diagram for the various components of FIGS. 6a and 6b.

In FIG. 6a and 6b, schematic drawings of the switching and sampling circuitry for the analog switches are shown. FIGS. 6a and 6b represent the delay and sample stages for the LED on LED off pulses, respectively. Power is supplied by +V (+5.8) at pin 16 on both one-shot monostable multivibrators, U4 and U5. The delay circuits are necessary for sampling the photodiode pulse at U6-6 during the middle of the LED on interval and LED off interval. The arrow on each of the integrated circuits U4A, U4B, U5A, U5B indicates on which polarity the one-shot is activated, either on the leading edge of the waveform or on the trailing edge of the waveform. Resistors R7-10 and capacitors C5-8 are used to provide the necessary time delays and sampling periods to the analog switches. The time delays and sampling periods to the analog switches are shown in FIG. 6c.

Figure 7:
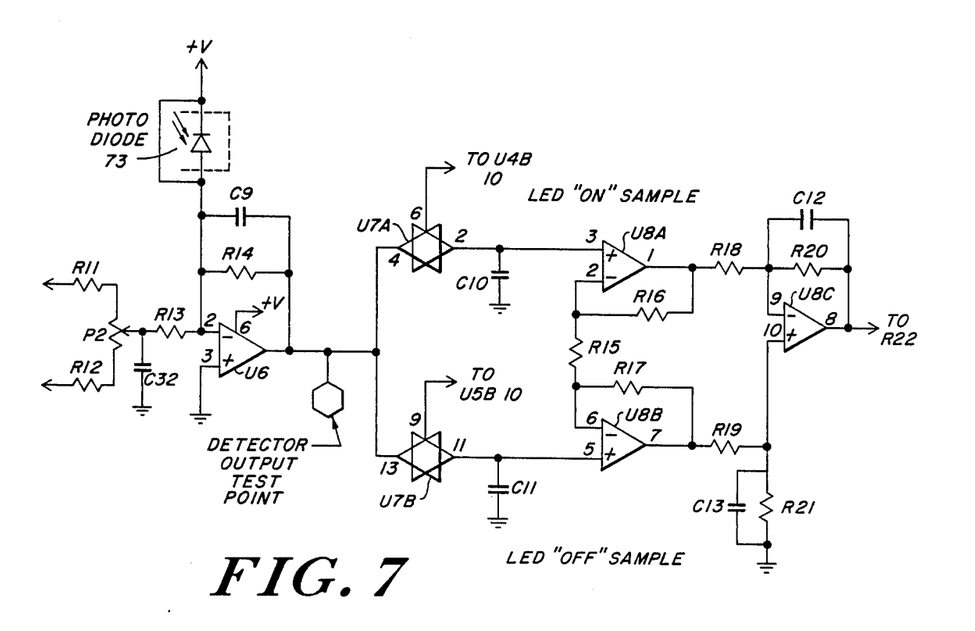
FIG. 7 is a schematic diagram of the synchronous demodulation and ambient light cancellation circuitry.

FIG. 7 describes the synchronous demodulator and ambient light cancellation circuitry. The output at integrated circuit U6-6 is the amplified 5% duty cycle reflectance signal from the photodiode in FIG. 5., and filtered by resistor R14 and capacitor C9. FIG. 6c also shows the sampling and delay periods to the analog switches U7A and U7B. The photodiode detector 73, receives the LED radiation reflected off the skin. In the illustrated embodiment a photodiode is utilized rather than a phototransistor because the photo-transistor, despite its high gain, has a non-linear light to output current relationship and this can produce an undesirable error in an environment having fluctuating ambient light levels. The photodiode, on the other hand, has a relatively linear light to output current relationship.

In reflection-mode, a large signal attenuation is typically observed. At a peak LED current of 25 mA, about 1.3 mW peak infrared power is radiated into the skin while only a few microwatts peak typically is received by the photodiode, which produces a peak signal current of less than one microampere. In the illustrated embodiment of FIG. 7, the signal is first amplified by current-to-voltage converter U6 using a low noise LM308 operations amplifier. Values for first Resistor R14 and capacitor C9 can be chosen to attenuate the high frequency noise in the signal without allowing integration of the signal pulse to take place. A potentiometer P2 can be employed to offset the signal so as to prevent the signal from approaching the saturation voltage. In the illustrated circuit the resulting output from U6-6 is a 4 ms pulse with a peak voltage of approximately −40 mV which is input to the analog switches U7A-4 and U7B-13.

The signal during the LED on interval is stored on capacitor C10 and the signal during the LED off interval is stored on capacitor C11. A differential amplifier U8A-C amplifies only the difference in voltage between capacitors C10 and C11. An instrumentation differential amplifier preferably is employed because of the high impedance characteristics which prevents any significant discharge of the capacitors storing the waveform pulses. Since ambient light level changes will produce only a level shift in the pulse signal, such changes are effectively cancelled by the synchronous detection and ambient light cancellation circuit in FIG. 7.

Figure 8:
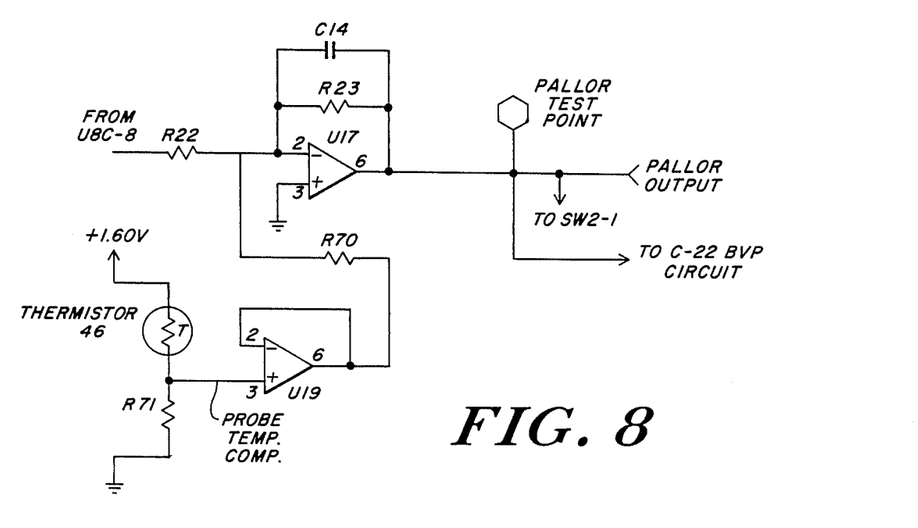
FIG. 8 is a schematic diagram of the temperature compensating thermistor circuitry.

FIG. 8 is a schematic diagram of the temperature compensation circuitry for the pallor signal. The pallor signal (the waveform from the synchronous detection and ambient light cancellation circuit) is compensated with the signal from the thermistor 46. The value of R70 should be selected to cancel LED temperature effects as detected by the thermistor 46. The temperature-compensated signal is then amplified and low pass filtered by integrated circuit U17. The pallor signal can then be sent to a readout device to display the degree of pallor (or blushing). This signal is also used to produce the average BVP signal.

Figure 9:
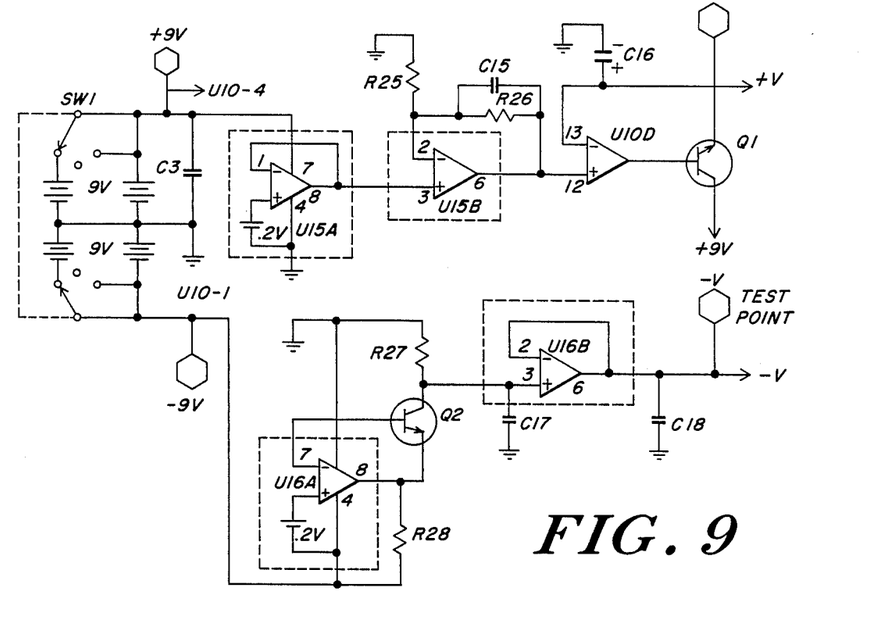
FIG. 9 is a schematic diagram of the power supply circuitry.

FIG. 9 shows the circuit diagram of the voltage regulators for the positive and negative supply voltages. The operation of the positive regulator is described first. U15A and U15B comprise a low current LM10CH integrated circuit which contains an internal 0.2 volt reference available at pin 4 as symbolized by the battery 0.2 in FIG. 9. U15A is wired as a voltage follower to buffer the +0.2 V reference for input to U15B. U15B is wired as a non-inverting amplifier to boost the +02 V to +5.8 V nominal, by the action of gain setting resistors R25 and R26. C15 acts to stabilize the circuit. The +5.8 V output from U15B is buffered by op amp U10D and transistor Q1, since neither U15B nor U10D alone supply the nominal 25 mA peak current pulses drawn by the monitor circuitry. C16 and C31 filter out noise on the +5.8 V supply caused by the LED current pulses.

The negative supply voltage regulator also employs an LM10CH integrated circuit, but in a slightly different configuration. U16A buffers the +0.2 V reference and outputs it across R28, which acts as a current source for transistor Q2. Q2 drives this current through R27 to produce the negative supply voltage, −5.8 V nominal. U16B, an op amp voltage follower buffers the output of Q2. C17 and C18 filter the negative supply voltage and prevent the circuit from self oscillating.

Figure 10:
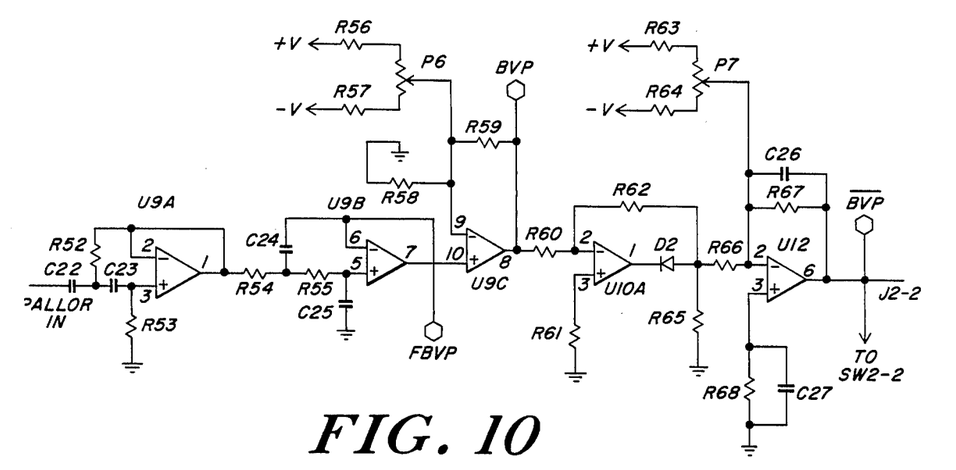
FIG. 10 is a schematic diagram of the circuitry to produce the BVP signal from the pallor signal.

FIG. 10 is a schematic diagram of a circuit for obtaining the average blood volume pulse amplitude, BVP, from the pallor signal, through filtering and rectifying of the pallor signal. In the illustrated embodiment the pallor signal is high pass filtered at approximately 0.5 Hz by the first operational amplifier, U9A, by selecting the appropriate resistors R52 and R53 and the appropriate capacitors C22 and C23. The signal is then low pass filtered at 2.5 Hz through the second operational amplifier, U9B, again with the appropriate selection of capacitors C24 and C25 and resistors R54 and R55. The filtered BVP signal is thus band pass filtered to attenuate various ambient noise such as low frequency drift in the pallor signal and 60 Hz harmonic signals from lighting. The potentiometer, P6, is utilized to zero the signal from the filtered BVP so as to prepare the signal to be rectified by the fourth operational amplifier, U10A, and averaged with a 4 second time constant with the fifth operational amplifier to produce the average Blood Volume Pulse signal.

Figure 11:
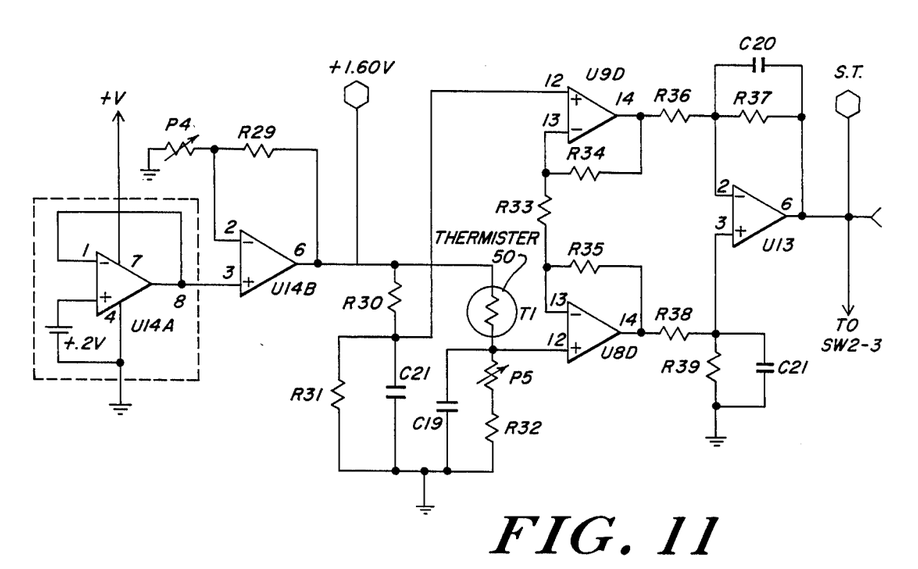
FIG. 11 is a schematic diagram of the thermistor and associated components to provide for the skin temperature signal.

FIG. 11 is a circuit diagram for a skin temperature thermometer. U14A and U14B comprise an LM10CLH integrated circuit. U14A buffers the +0.2 V reference which is amplified by U14B which is wired as a non-inverting amplifier. Gain setting resistors R29 and P4 boost the +0.2 V to precisely +1.60 V, which is the supply voltage for a thermistor bridge circuit. The bridge consists of resistors R30, R31, R32, and P5. The thermistor, T1 is part of the probe assembly, and sense facial skin temperature. The output voltage from the bridge is nearly linear over the 28 to 38 degree centrigrade range typically encountered on the skin and is input to an instrumentation amplifier consisting of op amps U8D, U9D, and U13. The bridge is balanced for zero volts output at 28 degrees centigrade by adjustment of trimpot, P5. The gain of the instrumentation amplifier is set by resistors R33 through R39 to be 12.2, so that the output range is 0 V to +2 V for the 28 to 38 degree centigrade range. Capacitors C20, C21, C19 and C28 filter out noise pulses picked up from the probe cable and monitor circuitry wiring.

Figure 12:
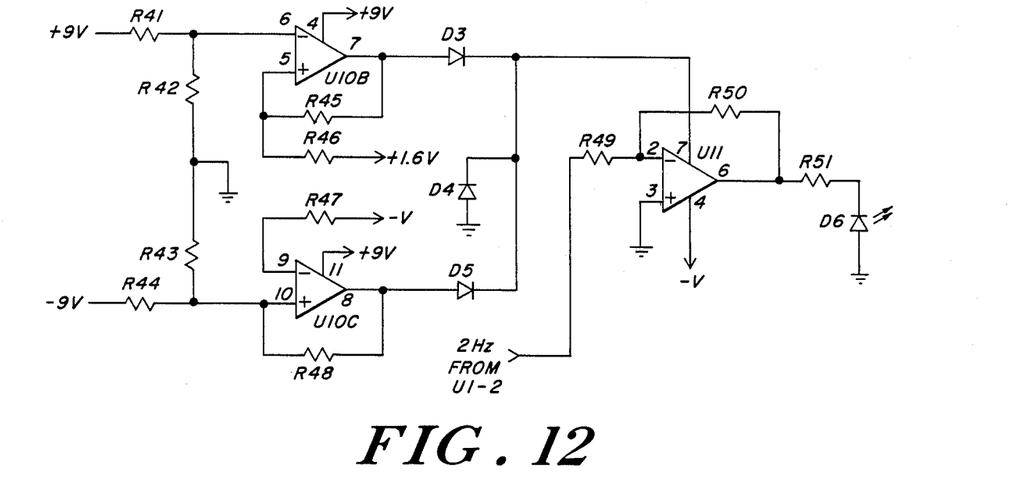
FIG. 12 is a schematic diagram of the circuit to detect a low battery voltage.

FIG. 12 shows the circuit which illuminates the panel battery low indicator when either the +9 V or −9 V battery output drops close to the minimum value necessary to operate the voltage regulator circuitry. The thresholds are set by R41 and R42 for the +9 V battery, and R44 and R43 for the −9 V battery. Op amps U10B and U10C are wired as comparators. When the battery voltages drop such that either the—input to U10B is less positive than +1.6 V, or the + input to U10C is less negative than −5.8 V (nominal) then the output of the respective op amp switches from about −5.8 V to about +5.8 V, thus activating op amp U11. Diodes D3, D4, and D5 gate the positive voltage from a triggered U10B or U10C to U11, and block the negative voltage from inactivated U10B or U10C. When U11 is activated by applying a positive voltage to its positive supply voltage input terminal, the 2 Hz pulses from oscillator, U1, are gated to the panel LED battery low indicator. Resistors R49, R50, and R51 effectively limit the LED current.

Figure 13:
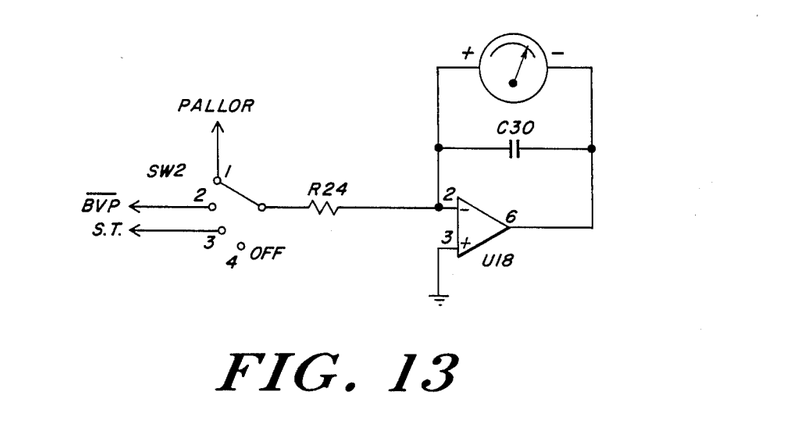
FIG. 13 is a schematic diagram of the meter driver and associated switch for the various outputs available.

FIG. 13 shows the meter driver circuit. The op amp, U18, acts as a current source for the panel meter. In the illustrated embodiment the meter should not be driven directly by the monitor circuitry since the maximum output signal voltage, which is +2 V, will not set the meter to full scale, due to its high coil resistance. Driving the meter from a current source also has the advantage that temperature related coil resistance changes will not affect the meter reading. Rotary switch, SW2, selects the desired signal (pallor, BVP, or skin temperature) to be displayed on the panel meter. An off position was supplied to eliminte the current drawn by the meter from the battery drain when the meter is not being read. Resistor R24 was selected to set the meter to a full scale reading for a +2 V input from the pallor, BVP, or skin temperature circuits.

Representative values for the components discussed herein are provided in Table I below:

TABLE I

| Capacitors, by component designation | | | |
|---|---|---|---|
| Designation | Value | Mfg. Part No. | Mfg. |
| C1 | 33 pF | CK05BX330K | Centralab |
| C2 | 10 pF | CK05BX100K | " |
| C3 | 0.01 uF | CK05BX103K | " |
| C4 | 100 pF | CK05BX101K | " |
| C5 | 0.001 uF | CK05BX102K | " |
| C6 | 0.001 uF | CK05BX102K | " |
| C7 | 0.01 uF | CK05BX103K | " |
| C8 | 0.001 uF | CK05BX102K | " |
| C9 | 220 pF | CK05BX221K | " |

TABLE I-continued

| C10 | 0.1 uF | CK05BX104K | " |
|---|---|---|---|
| C11 | 0.1 uF | CK05BX104K | " |
| C12 | 0.22 uF | CK06BX224K | " |
| C13 | 0.22 uF | CK06BX224K | " |
| C14 | 1.0 uF | CK06BX105K | " |
| C15 | 0.01 uF | CK05BX103K | " |
| C16 | 10 uF | 150D106X9010B2 | Sprague |
| C17 | 2 × 1.0 uF | CK06BX105K × 2 | Centralab |
| C18 | 47 uF | 150D476X9010R2 | Sprague |
| C19 | 0.22 uF | CK06BX224K | Centralab |
| C20 | 1.0 uF | CK06BX105K | " |
| C21 | 1.0 uF | CK06BX105K | " |
| C22 | 1.0 uF | CK06BX105K | " |
| C23 | 1.0 uF | CK06BX105K | " |
| C24 | 0.1 uF | CK05BX104K | " |
| C25 | 0.047 uF | CK05BX473K | " |
| C26 | 2 × 1.0 uF | CK06BX105K × 2 | " |
| C27 | 0.22 uF | CK06BX224K | " |
| C28 | 0.22 uF | CK06BX224K | " |
| C29 | 33 pF | CK05BX330K | " |
| C30 | 0.1 uF | CK05BX104K | " |
| C31 | 1.0 uF | CK05BX105K | " |
| C32 | 1.0 uF | CK05BX105K | " |

| Resistors, By Component Designation: | |
|---|---|
| Designation | Value |
| R1 | 470K |
| R2 | 22 M |
| R3 | 56K |
| R4 | 100K |
| R5 | 47K |
| R6 | 27 |
| R7 | 120K |
| R8 | 150K |
| R9 | 750K |
| R10 | 470K |
| R11 | 47K |
| R12 | 47K |
| R13 | 20K |
| R14 | 100K |
| R15 | 1K |
| R16 | 1K |
| R17 | 1K |
| R18 | 100K |
| R19 | 100K |
| R20 | 100K |
| R21 | 100K |
| R22 | 1K |
| R23 | 100K |
| R24 | 3.9K |
| R25 | 1.96K* |
| R26 | 56.2K* |
| R27 | 56.2K* |
| R28 | 1.96K* |
| R29 | 4.99K |
| R30 | 10.0K |
| R31 | 10.0K |
| R32 | 3.40K |
| R33 | 1.47K |
| R34 | 8.25K |
| R35 | 8.25K |
| R36 | 100K |
| R37 | 100K |
| R38 | 100K |
| R39 | 100K |
| R41 | 1 M |
| R42 | 287K |
| R43 | 1 M |
| R44 | 100K |
| R45 | 10 M |
| R46 | 1K |
| R47 | 1K |
| R48 | 10 M |
| R49 | 100K |
| R50 | 100K |
| R51 | 4.7K |
| R52 | 220K |
| R53 | 430K |
| R54 | 910K |
| R55 | 910K |
| R56 | 47K |
| R57 | 47K |

TABLE I-continued

| | | |
|---|---|---|
| R58 | 1K | |
| R59 | 10K | |
| R60 | 4.7K | |
| R61 | 1.1K | |
| R62 | 2.7K | |
| R63 | 470K | |
| R64 | 470K | |
| R65 | 10K | |
| R66 | 100K | |
| R67 | 2 M | |
| R68 | 91K | |
| R70 | 34.8K* | |
| R71 | 4.99K | |
| R72 | 100K | |
| R73 | 100K | |

Potentiometers and Trimpots:

| Designation | Value | Vendor |
|---|---|---|
| P1 | 100 ohm, 10 turn | Allied 521-3101 |
| P2 | 10K trim | Allied 822-2241 |
| P3 | 50K trim | Allied 822-2253 |
| P4 | 2K trim | Allied 822-2232 |
| P5 | 5K trim | Allied 822-2238 |
| P6 | 10K trim | Allied 822-2241 |
| P7 | 50K trim | Allied 822-2253 |

| Designation | Type | Manufacturer |
|---|---|---|
| Integrated Circuits, by component designation: | | |
| U1 | CD4060BMJ | National (RCA,F) |
| U2 | CD4528BMJ | National (F) |
| U3 | HA2-2705-5 | Harris |
| U4 | CD4528BMJ | National |
| U5 | CD4528BMJ | National |
| U6 | LM308H | National |
| U7 | HI1-0305-5 | Harris |
| U8 | OP-420HY | PMI |
| U9 | OP-420HY | PMI |
| U10 | OP-420HY | PMI |
| U11 | HA2-2705-5 | Harris |
| U12 | LM308 | National |
| U13 | LM308 | National |
| U14 | LM10CLH | National |
| U15 | LM10CH | National |
| U16 | LM10CH | National |
| U17 | LM308 | National |
| U18 | HA2-2705-5 | Harris |
| U19 | HA2-2705-5 | Harris |
| Diodes and Transistors by Component Designation | | |
| Q1 | 2N1304 | Etco |
| D1 | 1N4148 | F |
| Q2 | 2N2222 | Etco |
| D2 | 1N4148 | F |
| D3 | 1N3592 | ITT |
| D4 | 1N3592 | ITT |
| D5 | 1N3592 | ITT |
| D6 | LED TLR-107 | TI |
| S1 | SPX-5004-1 | Spectronics |
| Thermistors | | |
| 46 | UUA35J1 | Fenwal |
| 50 | UUA35J1 | Fenwal |
| Electronic Oscillator | | |
| 66 | GX1V | Statek |
| Double Stick Tape | | |
| 13 | 2181 | 3 M |

*selected component value

The invention has been described in connection with certain preferred embodiments which include simultaneous measurements of BVP and skin temperature; however, it should be clear that various changes and modifications can be made without departing from the spirit or scope of the invention. For example, various electronic modifications can be made to reduce the overall chip count. The demodulation scheme for subtracting artifact signals can be simplified and active temperature compensation in some circumstances can be avoided altogether by carefully selecting the components. Additionally, various changes can be made in the temperature compensation scheme such as incorporating a compensating resistance into the probe assembly, itself, rather than the monitor electronic hardware. Alternatively, a heater circuit, built into the transducer, can be used to stabilize the temperature.

Although the described embodiment is battery-powered and designed to have low power consumption for monitoring an ambulatory patient, similar devices can also be designed to make use of public utility voltages in hospital and home settings.

Moreover, the LED transmitters employed in the invention can be modified to emit at particularly useful wavelengths. For example, a properly-doped LED can be chosen to emit a wavelength of light corresponding to one of the isobestic wavelengths of hemoglobin, thus rendering the instrument insensitive to the blood oxygen content in the vascular system.

We claim:

1. A pallor and blush monitor for measuring changes in blood circulation of a patient's skin, the monitor comprising
   (a) transmitter means, adapted for positioning upon the patient's skin, for transmitting infrared radiation to a defined area of the skin;
   (b) pulsed power means, connected to the transmitter means, for pulsing the radiation from the transmitter means;
   (c) detector means, also adapted for positioning upon the skin, for detecting infrared radiation reflected by the defined area and generating electrical signals responsive thereto;
   (d) synchronous demodulator means, connected to the detector means, for receiving signals generated by the detector means when the transmitter means is on and off, and for producing an amplified difference signal from said detector-generated signals;
   (e) current regulating means for controlling the amplitude of the current drawn by the transmitter means; and
   (f) temperature compensating means, connecting to the synchronous demodulator means, said temperature compensating means including a thermistor located in proximity to the transmitter means for measuring changes in the temperature of the transmitter and a means for temperature compensating the amplified difference signal in response to the output of the thermistor.

2. The monitor of claim 1 wherein the transmitter means comprises a light emitting diode.

3. The monitor of claim 1 wherein the transmitter means comprises a GaAs light emitting diode.

4. The monitor of claim 1 wherein the transmitter means comprises a means for transmitting radiation at a wavelength in range corresponding to an isobestic wavelength of hemoglobin.

5. The monitor of claim 1 wherein the pulsed power means comprises a electronic oscillator.

6. The monitor of claim 1 wherein the pulsed power means comprises a electronic oscillator operating at a frequency of about 150 hertz or above.

7. The monitor of claim 1 wherein the detector means comprises a photodiode.

8. The monitor of claim 1 wherein the synchronous demodulator means further comprises a means for converting said electrical signals from the detector means into voltages.

9. The monitor of claim 8 wherein the synchronous demodulator means further comprises a first capacitance means for storing the signal from the detector means as a first voltage when the transmitter means is on, second capacitance means for storing the signals from the detector means as a second voltage when the transmitter means is off and a differential amplifying means for ampplifying the difference between the first and second voltages.

10. The monitor of claim 1 wherein the monitor further includes a low pass filter which is electrically connected to the temperature compensating means to filter the temperature-compensated amplified difference signal.

11. The monitor of claim 1 wherein the monitor further includes pulse rate extraction means for extracting pulse amplitude signals from the amplified difference signal, the extraction means comprising a band pass filter and a rectifier.

12. The monitor of claim 1 wherein the monitor further comprises an adjustment means for varying the current to the transmitting means and thereby permitting adjustment of the sensitivity of the monitor for differences in patient's skin color and skin hemoglobin content.

13. A pallor and blush monitor for measuring changes in blood circulation of a patient's skin, the monitor comprising:
   (a) a light-emitting diode, adapted for positioning upon the patient's skin, for transmitting infrared radiation at an isobestic wavelength of hemoglobin to a defined area of the skin;
   (b) an oscillator-pulsed power source connected to the light-emitting diode for pulsing the radiation from the diode;
   (c) adjustment means connected between the power source and the light-emitting diode cojprising a potentiometer for varying the current to the light-emitting diode whereby the sensitivity of the monitor can be adjusted to the patient's natural skin color and skin hemoglobin content;
   (d) current regulating means connected between the power source and the light-emitting diode for controlling the amplitude of the current drawn by the light-emitting diode;
   (e) a photodiode detector, also adapted for positioning upon the patient's skin, for detecting radiation reflected by the defined area and generating an electrical current in response thereto;
   (f) a synchronous demodulator circuit, connected to the photodiode detector, comprising
      (i) converter means for converting the current from the detector into a voltage;
      (ii) first capacitance means for storing a first voltage from the detector when the light-emitting diode is on;
      (iii) second capacitance means for storing a second voltage from the detector when the light-emitting diode is off; and
      (iv) differential amplifying means for amplifying the difference between the first and second voltage to generate an amplified difference signal; and
   (g) temperature compensating means, connected to the synchronous demodulator circuit, comprising
      a thermistor located in close proximity to the light-emitting diode, means for temperature-compensating the amplified difference signal in response to the output of the thermistor; and
      a low pass filter for filtering the temperature-compensated signal.

* * * * *